United States Patent [19]
Balson

[11] 3,955,284
[45] May 11, 1976

[54] DISPOSABLE DENTAL DRILL ASSEMBLY

[76] Inventor: John E. Balson, Church Road, Devon, Pa. 19333

[22] Filed: Jan. 2, 1975

[21] Appl. No.: 537,960

[52] U.S. Cl. .................................... 32/27; 415/503
[51] Int. Cl.² ............................................ A61C 1/10
[58] Field of Search ............ 32/26, 27, 58; 415/503

[56] References Cited
UNITED STATES PATENTS

| | | | |
|---|---|---|---|
| 2,033,662 | 3/1936 | Witt | 32/27 |
| 2,799,934 | 7/1957 | Kern | 32/DIG. 1 |
| 2,945,299 | 7/1960 | Fritz | 32/27 |
| 3,128,988 | 4/1964 | Mandrocan | 32/DIG. 1 |
| 3,210,847 | 10/1965 | Prufer | 32/58 |
| 3,298,103 | 1/1967 | Maurer | 32/27 |
| 3,408,043 | 10/1968 | Williams et al. | 32/27 X |
| 3,593,425 | 7/1971 | Robinson | 32/58 |
| 3,624,905 | 12/1971 | Barsby | 32/27 |

FOREIGN PATENTS OR APPLICATIONS

| | | | |
|---|---|---|---|
| 257,419 | 3/1928 | Italy | 32/26 |
| 838,938 | 7/1949 | Germany | 32/27 |

*Primary Examiner*—Robert Peshock
*Assistant Examiner*—Jack Q. Lever
*Attorney, Agent, or Firm*—John W. Logan, Jr.

[57] ABSTRACT

A disposable dental drill assembly is disclosed in this application and includes a housing in which is rotatably carried a rotor member including a turbine blade configuration and which is fixed to the end of a dental burr. The housing is formed with interlock means cooperating with complimentary means formed on a handle member whereby the drill assembly is easily removable from the handle member and can be replaced when the burr wears out. Both the housing and handle are formed with air passages and the handle is connected to a source of air pressure so that air flows over the turbine blades driving the rotor member and, accordingly, the burr. Because the drill assembly is disposable, the housing and the rotor member, including the turbine blade configuration, are made of a relatively inexpensive plastic material which can also be utilized for the handle member.

29 Claims, 11 Drawing Figures

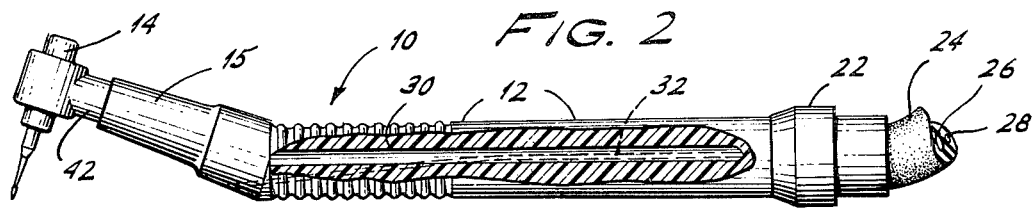
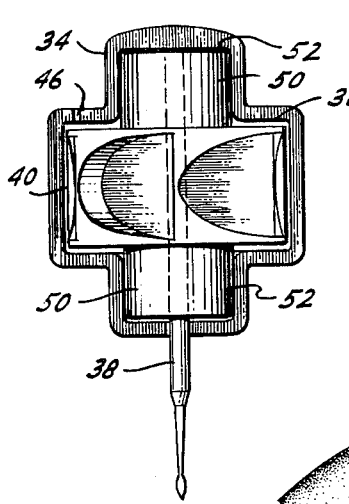
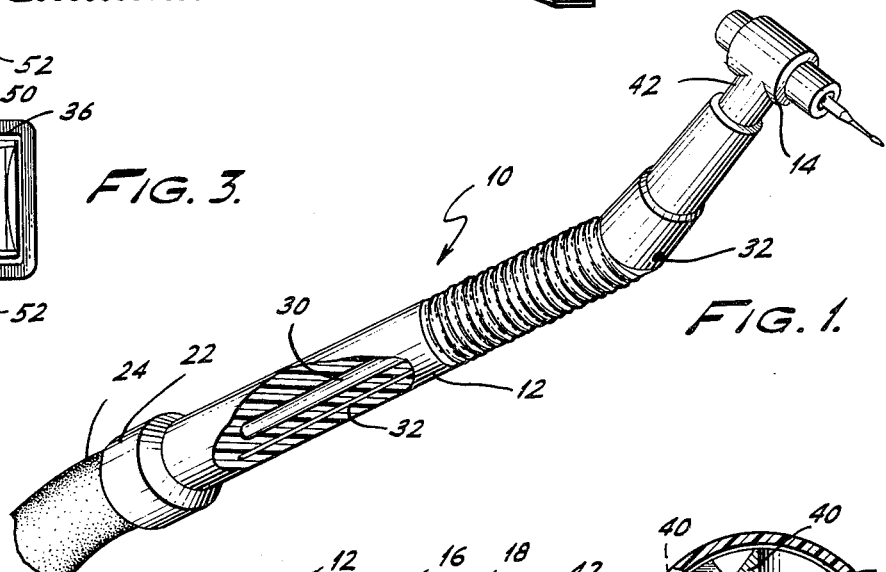
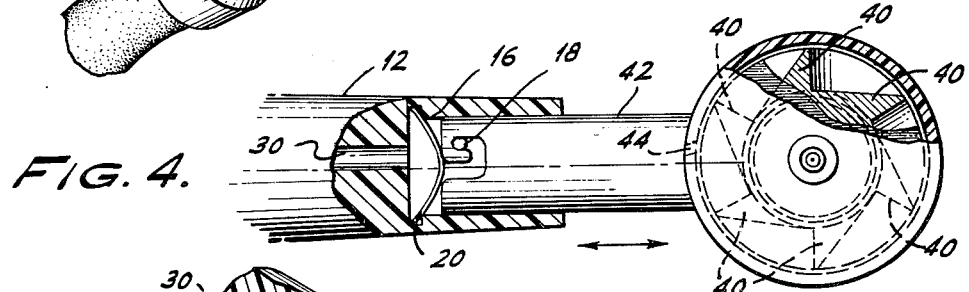
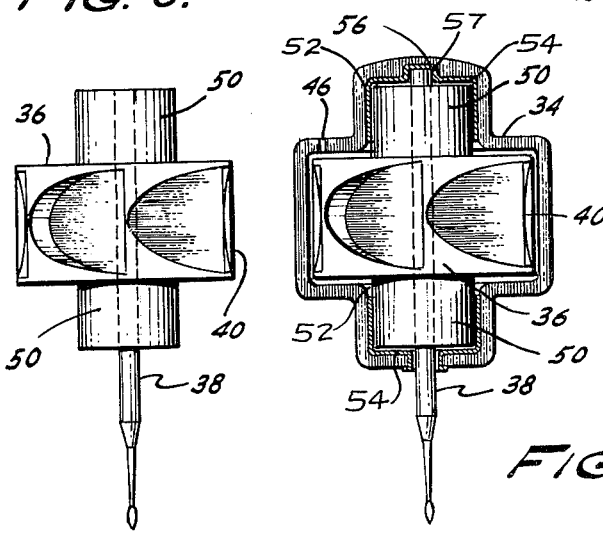
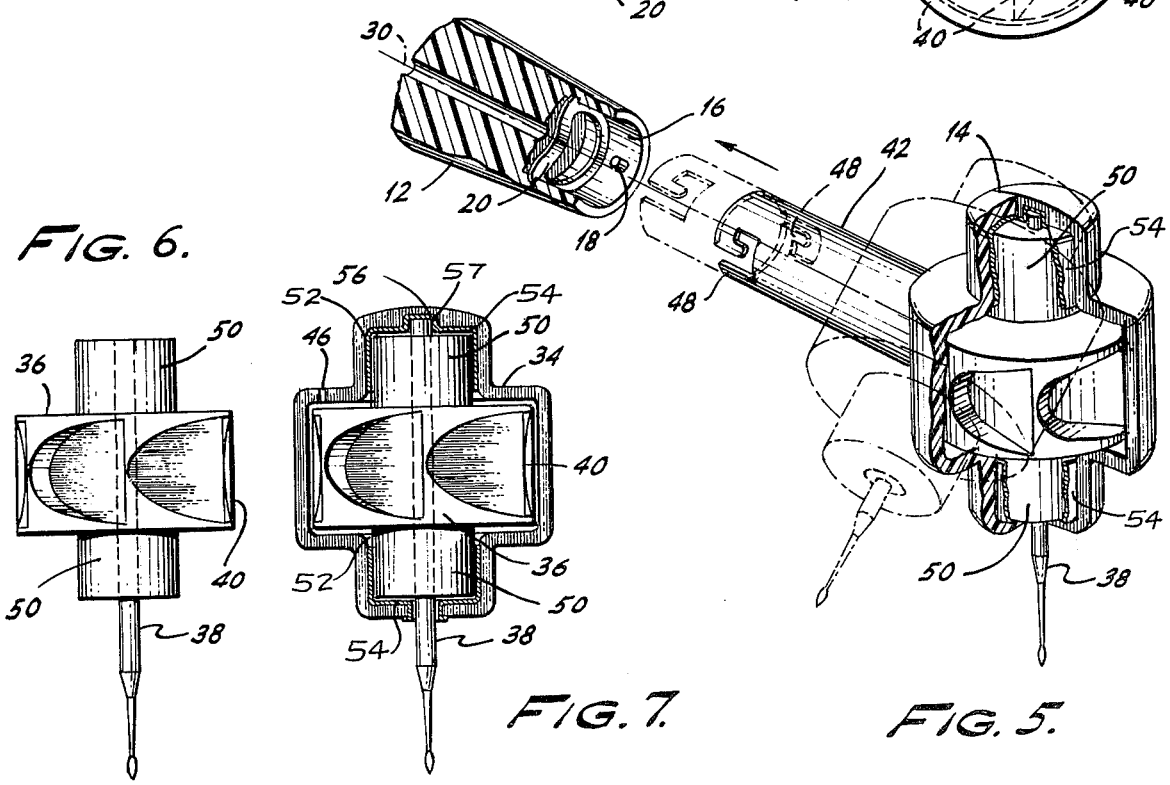
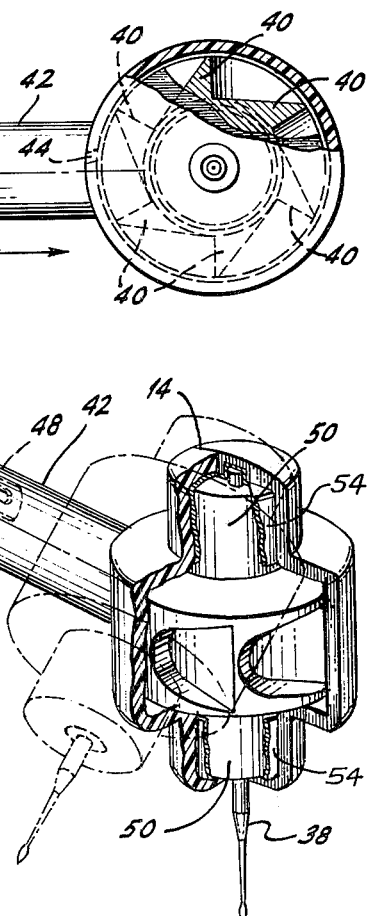

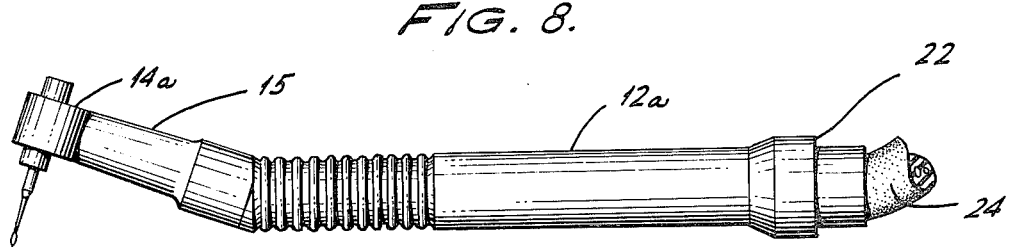
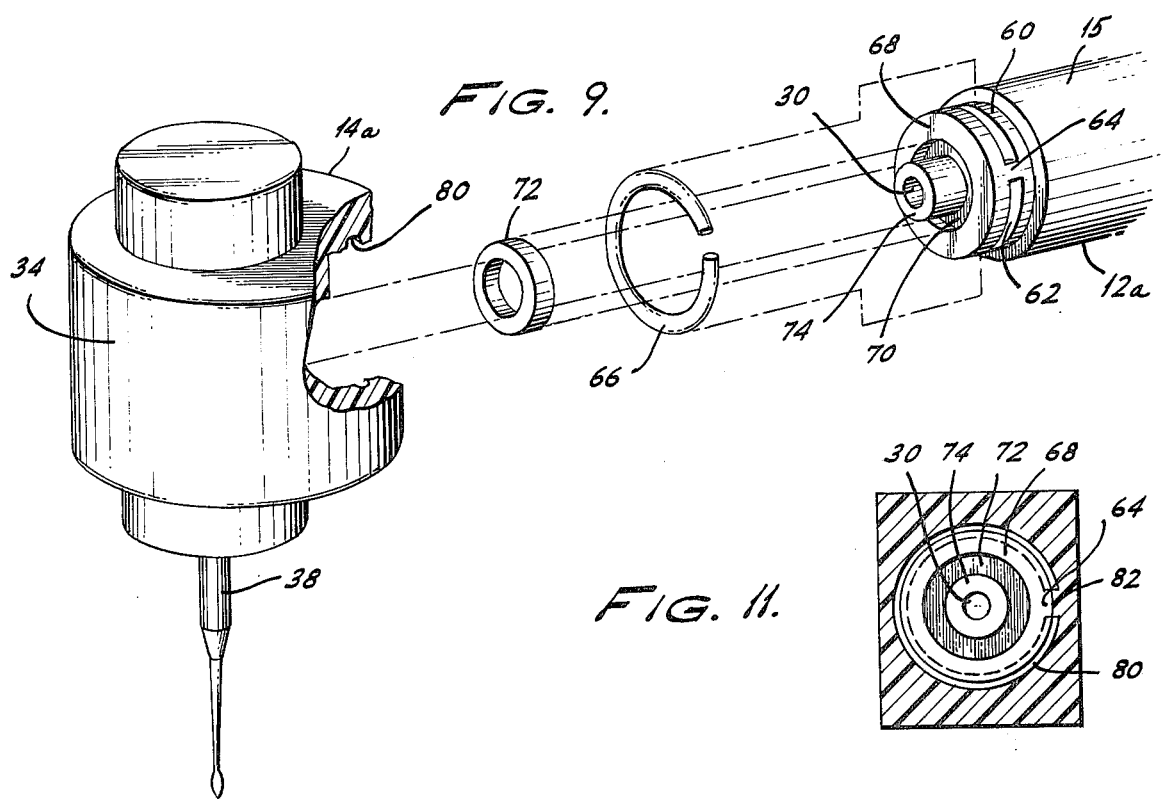
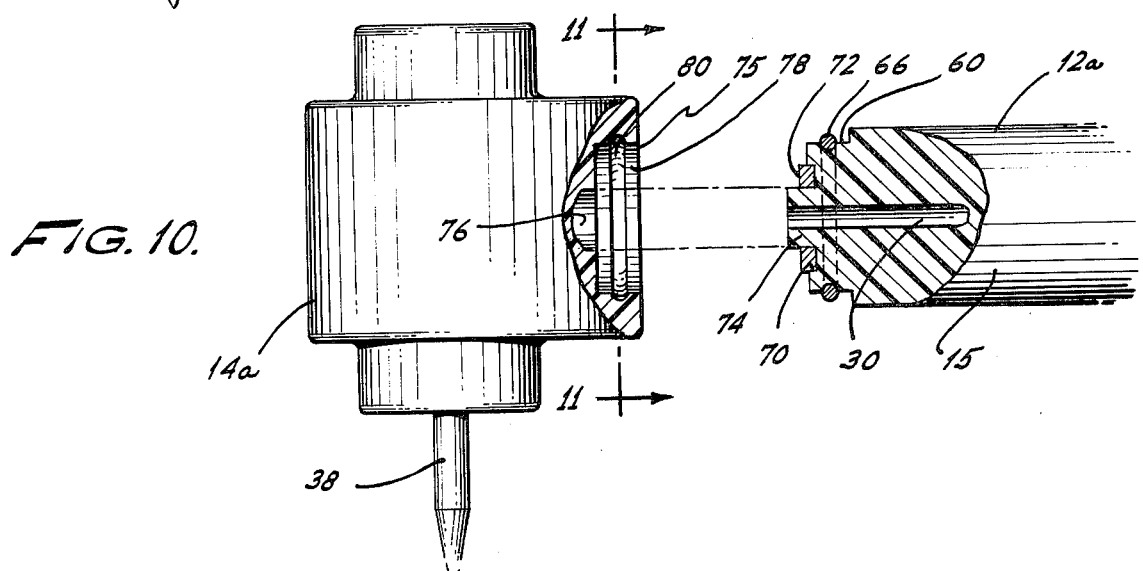

DISPOSABLE DENTAL DRILL ASSEMBLY

This invention relates to dental handpiece assemblies and, more particularly, to dental handpiece assemblies including a disposable dental drill assembly that is readily removable from a handle member for replacement.

Conventional dental handpieces of the type widely used today include a handle, one end of which is connected by a flexible conduit to a dental stand including sources of air and water and the other end of which is formed with an integral or otherwise permanently connected housing. The inside of the housing carries a plurality of bearing assemblies, usually of the ball bearing or similarly expensive type, in which is rotatably mounted a rotor member including a turbine blade configuration and a collet or similar arrangement for removably carrying a dental burr. An air passage is formed in the handle and communicates with the interior of the housing and the source of air so that the rotor member and, accordingly, the burr can be driven by air flow over the turbine blade configuration.

Handpieces of the type described above are generally made of costly metals or metal alloys such as aluminum and brass or nickel-silver and are generally made by costly machining techniques. When the cost of the rotor member, also made of costly metal, the collet and the bearing arrangement are added to the material and machining costs, it can be seen that these handpieces are relatively expensive devices.

In actual use the burr is driven at high speeds and has a relatively short useful life of only several hours after which it is replaced and disposed of. Of course, to provide the noted high speeds, the rotor member must be driven at correspondingly high speeds and, thus, the bearing assemblies between the rotor member and the housing also have a relatively short useful life, usually of only several months. When the bearing assemblies wear out, it is usual to remove the handle from the flexible conduit and send it out for repair or trade it in for a new one. Repair services are relatively expensive as is the purchase of a new handle, even with a trade-in allowance. Adding to the cost caused by the wearing out of bearing assemblies is the requirement of having a replacement handle which is used during the interim period when the worn out handle is being serviced or while waiting for delivery of a new handle. Obviously, this requirement necessitates the initial purchase of a plurality of expensive handles.

It is an object of this invention, therefore, to provide a relatively low cost dental handpiece that is economical to operate and maintenance free.

It is another object of this invention to provide a relatively low cost, self-contained disposable dental drill assembly which may easily be removed from a handle and replaced.

It is yet another object of this invention to provide a relatively low cost maintenance free handle usable in a dental handpiece.

Finally, it is an object of this invention to provide an economical dental handpiece including a relatively inexpensive handle and a disposable self-contained dental drill assembly.

These and other objects of this invention are accomplished by providing a dental handpiece including a self-contained dental drill assembly and a handle. The dental drill assembly includes a housing made of relatively inexpensive plastic material and formed with an air inlet passage and interlock means cooperating with interlock means on the handle for removably coupling the drill assembly to the handle. Rotatably mounted in the housing is a rotor member also made of relatively inexpensive plastic material and formed with a turbine blade configuration. One end of a dental burr is fixedly carried by the rotor member and the other end extends outwardly from the housing. The handle is a generally cylindrical member formed with an offset neck portion, the end of which includes the interlock means. Formed on the other end of the cylindrical member is additional coupling means for attaching the handle to a source of air pressure and formed through the cylindrical member is an air passage whereby air can flow from the source through the handle and the air passage in the housing of the drill assembly to the turbine blade configuration driving the rotor member and the burr. Preferably the handle is also formed of a relatively inexpensive plastic material.

For a better understanding of the invention, reference is made to the following description of preferred embodiments thereof taken in conjunction with the figures of the accompanying drawing, in which:

FIG. 1 is a perspective view of a dental handpiece assembly in accordance with this invention;

FIG. 2 is a side view, partly in section, of the dental handpiece assembly illustrated in FIG. 1;

FIG. 3 is a partial sectional view of a dental drill assembly in accordance with the invention and taken along the line 3—3 of FIG. 2;

FIG. 4 is a sectional view of a dental drill assembly in accordance with this invention and taken generally along the line 4—4 of FIG. 1;

FIG. 5 is an exploded perspective view with parts thereof broken away and illustrating a suitable interlocking coupling between a dental drill assembly and a handle in accordance with this invention;

FIG. 6 is a front elevational view of a rotor member usable with a dental drill assembly in accordance with this invention;

FIG. 7 is a partial sectional view similar to FIG. 3 illustrating a different embodiment of the invention;

FIG. 8 is a side view of another embodiment of a dental handpiece assembly in accordance with this invention;

FIG. 9 is an exploded perspective view of the dental handpiece assembly illustrated in FIG. 8 with parts thereof broken away;

FIG. 10 is an enlarged side view of the dental handpiece assembly illustrated in FIG. 8 with parts thereof broken away; and FIG. 11 is an end view along the line 11—11 of FIG. 10.

Referring briefly to FIGS. 1 and 2 of the drawing, there is illustrated a dental handpiece 10 in accordance with this invention including a handle 12 and a disposable dental drill assembly 14 which, as will be fully explained hereinafter, is removably secured to the handle. In accordance with one aspect of this invention, the handle 12 includes a generally cylindrical member having a neck portion 15 extending at an angle from the end adjacent the drill assembly 14 and is made of a suitable plastic material by conventional molding techniques. As used in this application, the term "plastic" means any synthetic or natural organic material which may be shaped when soft and then hardened and may include, by way of example, various resins, resinoids, polymers, cellulose derivatives, casein materials and protein.

As best seen in FIG. 5 of the drawing, the neck 15 of the handle 12 is formed with a counterbore 16, the cylindrical wall portion of which is formed with a plurality of inward projections 18, only one of which is shown, forming part of an easily removable interlocking connection between the handle and the disposable drill assembly 14. As will be made clearer hereinafter, it may be desirable to provide a spring washer 20 seated in the bottom surface of the counterbore 16 for assuring the integrity of the connection between the handle and the drill assembly. At the end opposite the neck 15 and the drill assembly 14, the handle 12 is formed with a coupling means 22 which may be in the form of an internally threaded counterbore or collar or an externally threaded stem and the coupling means cooperates with a mating configuration formed on a flexible conduit 24 to connect the handle to the conduit. The coupling means 22 is rather conventional and is, therefore, not specifically illustrated in the drawing. The flexible conduit 24 is connected to a generally conventional dental stand (not shown) including an air compressor means and a water pump. Air and water passages 26 and 28, respectively, are formed in the conduit 24 and communicate appropriately with the air compressor and the water pump. Formed through the handle 12 are suitable air and water passages 30 and 32, respectively, which communicate at one end with the air and water passages 26 and 28, respectively, in the conduit 24. The other end of the air passage 30 in the handle 12 terminates in the neck 15 and communicates with the counterbore 16 and, thus, as will be made clear, with the dental drill assembly 14; the other end of the water passage 32 in the handle 12 terminates in the outer surface of the neck 15 so that it directs the flow of water to the actual working surface of the dental drill assembly 14 for cooling purposes. it should be understood that other fluids could be utilized in place of water and that the water passage 32 could terminate with a nozzle configuration.

Referring to FIGS. 3 through 5 of the drawing, a preferred embodiment of the disposable dental drill assembly 14 is illustrated and includes a housing 34 in which is rotatably carried a rotor member 36 which member fixedly carries one end of a dental burr 38. Both the housing 34 and the rotor member 36 are formed of a suitable plastic material by generally conventional molding techniques. Since the rotor member 36 is carried in the housing 34, the latter is formed in two parts which can be seamed together or frictionally joined after insertion of the rotor member. While various techniques can be utilized to secure the burr 38 to the rotor member 36, a preferred technique is to mold the rotor member about the end of the burr. In carrying out the preferred technique, it may be desirable to form the end of the burr 38 with grooves and/or radial shoulders to assure that relative movement between the burr and the rotor member is prevented.

The rotor member 36 is molded or otherwise formed with a plurality of turbine blades 40 which may have any suitable configuration and which are driven by the air flow from the compressor to rotate the burr 38. Thus, the housing 34 is formed with a hollow cylindrical extension 42 extending radially therefrom and is also formed with an air passage 44 communicating with the interior of the extension which is received in the counterbore 16 in the handle 12 when the handpiece is assembled. Air from the compressor flows through the air passages 28 and 30, the counterbore 16, the interior of the extension 42, air passage 44 and against the turbine blades 40. The housing 34 can be formed with an opening 46 which vents the air to the atmosphere and prevents the buildup of air pressure in the housing 34 or the opening in the housing through which the burr 38 extends could be slightly enlarged to provide for venting the air.

Referring to FIG. 5 of the drawing, it can be seen that the cylindrical extension 42 is formed at its free end with a plurality of bayonet type slots 48 which cooperate with the projections 18 in the counterbore 16 to removably connect the dental drill assembly 14 to the handle 12. To assemble the drill assembly 14 to the handle 12, the drill assembly is oriented as shown in phantom lines in FIG. 5 of the drawing such that the free ends of the slots 48 are aligned with the projections 28 and the extension 42 is pushed into the counterbore 16 against the spring washer 20. Thereafter, the drill assembly 14 is rotated to the position illustrated by the solid lines such that the projections 28 are adjacent the closed ends of the slots 48. The drill assembly 14 is released and the spring washer 20 biases the drill assembly outwardly from the counterbore 16 maintaining engageement between the projections 18 and the slots 48. If desired, a suitable seal arrangement could be included between the drill assembly 14 and the handle 12 to prevent the leakage of air. While a bayonet type of connection between the dental drill assembly 14 and the handle 12 is disclosed in this application, it should be understood that various other quick-disconnect interlocking means could be utilized. In view of the foregoing it should be understood that when the burr 38 wears out the dental drill assembly 14 is removed from the handle 12 by rotating the drill assembly back to the phantom line position and allowing the spring washer 20 to eject it from the handle. A new dental drill assembly is connected to the handle and the worn out drill assembly is disposed of.

Since the useful life of the drill assembly 14 is relatively short, inexpensive bearing arrangements can be utilized between the rotor member 36 and the housing 34. In the form of the invention illustrated in FIG. 3 of the drawing, the rotor member 34 includes molded or otherwise integrally formed stub shafts 50 extending axially from opposite sides of the rotor portion formed with the turbine blades 40. The stub shafts 50 are in slight bearing engagement with seats 52 molded or otherwise formed integral with the housing 34. As the rotor member 36 is driven, the stub shafts ride in the seats 52. The end surfaces of the stub shafts 50 can be in direct contact with the end walls of the seats 52 or can be slightly spaced therefrom such that they ride on a cushion of air. With the bearing arrangement thus described, the plastic materials utilized for the housing 34 and the rotor member 36 should be such that the heat generated during the rotation of the rotor member will not cause the members to fuse together. An example of a suitable type of material usable in the FIG. 3 embodiment is manufactured and sold by E. I. du Pont de Nemours & Co. under the trademark "Delrin" and which contains approximately 2% silicon and TFE.

Alternatively, as illustrated in FIG. 7 of the drawing, both the housing 34 and the rotor member 36 can be made of cheaper plastic materials and a suitable wear plate 54 can be inserted in each of the seats 52 so that direct engagement between the stub shafts 50 and the seats 52 is prevented. As also illustrated in the FIG. 7 embodiment, the end of the dental burr 38 can project slightly above the top stub shaft 50, and can bear on an additional seat 56 formed in the top seat 52, as seen in the drawing, to provide additional bearing engagement. It should be understood that the seat 56 could be used in the FIG. 3 embodiment and that when used with the FIG. 7 embodiment, the wear plate 54 used with the top seat 52, as seen in the drawing, includes a seat portion 57 that fits in the seat 56.

Referring to FIGS. 8 through 11 of the drawing, another embodiment of the invention including a handle 12a and a disposable dental drill assembly 14a is illustrated. Both the handle 12a and the drill assembly 141a are generally similar to the handle 12 and dental drill assembly 14 disclosed previously except that a different interlocking coupling arrangement between the handle and the drill assembly is disclosed. Accordingly, like reference numerals will be utilized for like parts. Similar to the handle 12, handle 12a is a generally cylindrical member having a neck portion 15 extending at an angle to the cylindrical member and is formed with air and water passages similar to passages 30 and 32, and a coupling means 22 for connection to the flexible conduit 24. At the end adjacent the neck portion 15, the handle 12a is formed with a reduced diameter, generally cylindrical tip 60 having a seat 62 in the form of a groove of semi-circular cross-section extending about its periphery intermediate its axial ends. The seat 62 terminates in opposite ends located adjacent an outer surface portion 64 of the tip and carries a compressible retaining ring 66 in the form of a split ring member having opposite ends located adjacent to and cooperating with the surface portion 64 to prevent rotation of the ring relative to the handle. Retaining ring 66 has a circular cross-section and is of a size such that a portion thereof projects radially around the tip 60 for engagement with the drill assembly 14a as will be made clear hereinafter.

In its free end face 68, the tip 60 is formed with a cylindrical recess or seat 70 in which is carried an annular sealing washer 72 and is further formed with a cylindrical boss 74 extending from the end face of the seat 70 outwardly beyond the end of the tip. The thickness of washer 72 is larger than the depth of seat 70 so that a portion of the washer projects beyond the end face 68 of the tip and the axial length of the boss 74 is larger than the thickness of the washer whereby the boss extends beyond the washer. As clearly illustrated in FIGS. 9 and 10 of the drawing, air passage 30 extends through the cylindrical portion of the handle and the neck 15, the tip 60 and the cylindrical boss 74.

The dental drill assembly 14a, similar to dental drill assembly 14, includes a housing 34 in which is rotatably carried a rotor member fixed to a dental burr 38. The rotor member is similar to rotor member 36 illustrated in FIG. 6 of the drawing and is formed with a turbine blade configuration 40 and, preferably, with stub shafts 50, 50 mounted in seats formed in the housing generally as illustrated in either FIGS. 3 or 7 of the drawing. Instead of cylindrical extension 42, however, the embodiment illustrated in FIGS. 8–11 of the drawing includes a circular opening 75 formed through the side wall of the housing 34 which cooperates with the tip 60 on the handle 12a to removably couple the handle 12a and the dental drill assembly 14a. The configuration of the opening 75 includes a bore 76 and a counterbore 78 with the diameter of the former being such that it snugly receives the cylindrical boss 74 formed on the tip 60. Intermediate the ends of the counterbore 78 is a seat 80 in the form of a groove of semi-circular cross-section which is of a size to receive the radially projecting portion of the retaining ring 66. The seat 80 is spaced from the bore 76 such that the sealing washer 72 on the handle 12a can fit between the end face of the counterbore 78 and also seat 80.

To assemble the dental drill assembly to the handle, the tip 60 is inserted in the opening 75 in the drill assembly causing the ring 66 to compress until it is radially adjacent the seat 80 where it expands to resist relative movement. At this point, the cylindrical boss 74 seats in the bore 76 allowing the passage of air to the turbine blade configuration and the sealing washer 72 bears against the end face of the counterbore 78 and seals the coupling against the leakage of air. In order to locate and properly orient the drill assembly 14a relative to the handle 12a and also to prevent relative rotation therebetween, a lug 82 is formed across the seat 80 and fits between the ends of retaining ring 66 bearing on the surface portion 64 of the tip 60. Once assembled, relative rotation between the handle and the drill assembly is resisted by the engagement between the lug 82 and the ends of the retaining ring 66, the relative rotation of which is prevented by the surface portion 64. Of course, the drill assembly 14a and the handle 12a cannot be coupled unless the lug 82 is oriented to fit between the ends of the retaining ring 66. Removal of the drill assembly 14a from the handle 12a is accomplished by pulling on the drill assembly with sufficient force to compress the ring.

With the coupling arrangement disclosed in FIGS. 8 and 9 of the drawing, the special configuration of the opening 75 in the housing 34 may necessitate that the wall thickness of the housing be larger than that of the drill assembly 12. This may be accomplished by merely enlarging the wall thickness throughout the circumferential extent of the housing 34, or by merely eccentrically locating the rotor in the housing as illustrated in FIGS. 8–11, or by providing a small thickened boss in the housing and forming the opening in the boss.

From the preceding description of the invention, it can be seen that an economical dental handpiece is provided which includes a relatively inexpensive, self-contained and disposable dental drill assembly removably coupled to a relatively inexpensive, maintenance-free handle. When it is desired to replace the drill assembly, either because the burr has worn out or a different burr is required for a particular dental procedure, it is easily removed from the handle and is easily replaced with a new assembly.

While in the foregoing several preferred embodiments of a disposable dental drill and a handle in accordance with this invention have been described, it should be understood that various modifications will be obvious to those skilled in the art and are within the scope of the invention as recited in the appended claims.

I claim:

1. A dental handpiece including a handle and a self-contained dental drill assembly, said dental drill assembly a housing and a rotor member rotatably including mounted therein, said rotor member being formed with turbine blades and being fixedly and non-removably secured to the end of a dental burr, said housing being removably connected to said handle by interlocking coupling means, said handle being formed with a passage in communication with a passage in said housing, said passage in said housing being arranged to direct a fluid against said turbine blades to rotate said rotor member.

2. A dental handpiece in accordance with claim 1 wherein said handle is formed with a counterbore and said dental drill assembly is formed with a cylindrical extension received in said counterbore.

3. A dental handpiece in accordance with claim 2 wherein said counterbore is formed with projections and said cylindrical extension is formed with slots in interlocking engagement with said projections.

4. A dental handpiece in accordance with claim 1 wherein said handle includes a compressible retaining ring and said dental drill assembly includes a seat in which said retaining ring is received to resist relative movement between said handle and said dental drill assembly.

5. A dental handpiece in accordance with claim 1 including seal means between said handle and said dental drill assembly.

6. A dental handpiece in accordance with claim 1 including locating means for orienting said dental drill assembly relative to said handle.

7. A dental handpiece in accordance with claim 1 wherein said housing and said rotor member are formed of plastic material.

8. A disposable self-contained dental drill assembly comprising a housing and a rotor member rotatably carried therein, said rotor member including turbine blade means and being fixedly non-removably secured to the end of a dental burr, said housing including interlocking means for removably coupling said dental drill assembly to a handle.

9. A disposable self-contained dental drill assembly in accordance with claim 8 wherein said means for removably coupling said dental drill assembly to a handle includes an extension integrally formed with said housing and which is adapted to retain said handle therewith.

10. A disposable self-contained dental drill assembly in accordance with claim 8 wherein said means for removably securing said dental drill assembly to a handle includes a portion of a bayonet coupling arrangement.

11. A disposable self-contained dental drill assembly in accordance with claim 8 wherein said means for removably securing said dental drill assembly to a handle includes an opening formed through said housing and being formed with an interlocking configuration.

12. A disposable self-contained dental drill assembly in accordance with claim 11 wherein said interlocking configuration comprises a groove.

13. A disposable self-contained dental drill assembly in accordance with claim 12 wherein a radially projecting lug extends across said groove.

14. A disposable self-contained dental drill assembly in accordance with claim 8 wherein said housing and said rotor member are formed of plastic material.

15. A disposable self-contained drill assembly in accordance with claim 8 wherein said rotor member includes a central portion on which said turbine blade means is formed and integral generally cylindrical stub shafts projecting axially from opposite sides of said central portion, and wherein said housing includes integrally formed, generally cylindrical seats in which said stub shafts are rotatably carried.

16. A disposable self-contained drill assembly in accordance with claim 15 wherein said stub shafts are in slight bearing engagement with said seats.

17. A disposable self-contained drill assembly in accordance with claim 15 wherein said stub shafts are slightly spaced from said seats whereby said stub shafts ride on a cushion of air when said rotor member is rotating.

18. A disposable self-contained drill assembly in accordance with claim 15 wherein a wear plate is located in said seats and is in slight bearing engagement with said stub shafts.

19. A dental handpiece in accordance with claim 1 wherein said rotor member is molded about the shank of said dental burr.

20. A disposable self-contained drill assembly in accordance with claim 8 wherein said rotor member is molded about the shank of said dental burr.

21. A dental handle including a generally cylindrical member formed with an offset neck portion at one end thereof, said neck portion being formed with coupling means for removably coupling said handle to a disposable drill assembly, the other end of said cylindrical member being formed with connecting means for connecting said handle to a flexible conduit, said coupling means including a reduced diameter tip extending from said neck portion, said tip including a peripheral groove intermediate its ends in which is carried a compressible retaining ring, an air passage extending through said handle from said other end of said cylindrical member to the end of said neck portion, and a water passage extending from said other end of said cylindrical member to the outer wall of said neck portion adjacent said end thereof.

22. A dental handle in accordance with claim 21 being made of plastic material.

23. A dental handle in accordance with claim 21 wherein a cylindrical boss extends from the free end of said tip and wherein a sealing washer seats on said boss adjacent said free end of said tip.

24. A dental handpiece including a handle and a self-contained dental drill assembly, said dental drill assembly including a housing and a rotor member rotatably mounted therein, said rotor member being formed with turbine blades and being fixedly secured to the end of a dental burr, said housing being removably connected to said handle by interlocking coupling means, said handle being formed with a passage in communication with a passage in said housing, said passage in said housing being arranged to direct a fluid against said turbine blades to rotate said rotor member, said handle being formed with a counterbore and said dental drill assembly being formed with a cylindrical extension received in said counterbore, said counterbore being formed with projections and said cylindrical extension being formed with slots in interlocking engagement with said projections.

25. A dental handpiece including a handle and a self-contained dental drill assembly, said dental drill assembly including a housing and a rotor member rotatably mounted therein, said rotor member being formed with turbine blades and being fixedly secured to the end of a dental burr, said housing being removably connected to said handle by interlocking coupling means, said handle being formed with a passage in communication with a passage in said housing, said passage in said housing being arranged to direct a fluid against said turbine blades to rotate said rotor member, said handle including a compressible retaining ring and said dental drill assembly including a seat in which said retaining ring is received to resist relative movement between said handle and said dental drill assembly.

26. A dental handpiece including a handle and a self-contained dental drill assembly, said dental drill assembly including a housing and a rotor member rotatably mounted therein, said rotor member being formed with turbine blades and being fixedly secured to the end of a dental burr, said housing being removably connected to said handle by interlocking coupling means, said handle being formed with a passage in communication with a passage in said housing, said passage in said housing being arranged to direct a fluid against said turbine blades to rotate said rotor member, and locating means for orienting said dental drill assembly relative to said handle.

27. A disposable self-contained dental drill assembly comprising a housing and a rotor member rotatably carried therein, said rotor member including turbine blade means and being fixedly secured to the end of a dental burr, said housing including interlocking means for removably coupling said dental drill assembly to a handle, said means for removably securing said dental drill assembly to a handle including an opening formed through said housing, said opening being formed with an interlocking configuration.

28. A disposable self-contained dental drill assembly in accordance with claim 27 wherein said interlocking configuration comprises a groove.

29. A disposable self-contained dental drill assembly in accordance with claim 28 wherein a radially projecting lug extends across said groove.

* * * * *

UNITED STATES PATENT OFFICE
CERTIFICATE OF CORRECTION

Patent No. 3,955,284                Dated May 11, 1976

Inventor(s) John E. Balson

It is certified that error appears in the above-identified patent and that said Letters Patent are hereby corrected as shown below:

Claim 8, column 7, line 4, after "fixedly" insert -- and --.

Signed and Sealed this

Twenty-eighth Day of September 1976

[SEAL]

Attest:

RUTH C. MASON
Attesting Officer

C. MARSHALL DANN
Commissioner of Patents and Trademarks